(12) United States Patent
Burtin et al.

(10) Patent No.: US 6,248,238 B1
(45) Date of Patent: *Jun. 19, 2001

(54) MEDICAL APPARATUS FOR THE EXTRACORPOREAL TREATMENT OF BLOOD OR PLASMA, AND PROCESSES FOR USING THIS APPARATUS

(75) Inventors: Jacques Burtin, Feyzin; Michel Thomas, Serezin du Rhone; Pierre Valette, Meyzieu, all of (FR)

(73) Assignee: Hospal Industrie, Meyzieu Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/845,142

(22) Filed: Apr. 21, 1997

(30) Foreign Application Priority Data

Apr. 19, 1996 (FR) .................................................. 96 05189
Jul. 19, 1996 (FR) .................................................. 96 09340

(51) Int. Cl.⁷ ............................ B01D 61/24; B01D 71/42
(52) U.S. Cl. ............... 210/646; 210/500.21; 210/500.24; 210/500.43; 210/645
(58) Field of Search ..................... 210/500.21, 500.24, 210/500.43, 645

(56) References Cited

U.S. PATENT DOCUMENTS

| 4,545,910 | 10/1985 | Marze | 210/651 |
| 5,236,592 | * 8/1993 | Dejardin et al. | 210/646 |
| 5,417,981 | * 5/1995 | Endo et al. | 424/486 |

FOREIGN PATENT DOCUMENTS

| 28 12 174 | 9/1978 | (DE) . |
| 0 561 379 | 9/1993 | (EP) . |
| 0 568 451 | 11/1993 | (EP) . |
| 96/022288 | 2/1996 | (WO) . |

* cited by examiner

Primary Examiner—John Kim
(74) Attorney, Agent, or Firm—Millen, White, Zelano & Branigan, PLC.

(57) ABSTRACT

A medical apparatus for the extracorporeal treatment of blood or plasma comprises a semi-permeable membrane consisting of at least one electronegative polymer, such that the surface of the semi-permeable membrane has negative electric charges. Before the sterilization of the apparatus, and before or after the formation of the membrane, at least one cationic and anti-protease agent is incorporated in at least one part of the membrane, this agent undergoing bulk adsorption or semi-bulk adsorption in the membrane and/or being bound by an ionic interaction with the electronegative sites of the membrane.

17 Claims, 5 Drawing Sheets

MEDICAL APPARATUS FOR THE EXTRACORPOREAL TREATMENT OF BLOOD OR PLASMA, AND PROCESSES FOR USING THIS APPARATUS

The present invention relates to a medical apparatus for the extracorporeal treatment of blood or plasma, by means of which apparatus it is possible to prevent the adverse consequences of activation of the contact phase. The present invention also relates to processes for producing a medical apparatus for the extracorporeal treatment of blood or plasma, by means of which apparatus it is possible to prevent the adverse consequences of activation of the contact phase, these consequences being known under the name of anaphylactoid reactions.

Anaphylactoid reactions sometimes occur in patients undergoing various forms of treatment of the blood via extracorporeal circulation. These reactions manifest themselves several minutes after the start of the treatment in the form of various symptoms, including a general sensation of heat, numbness of the fingers, lips or tongue, shortness of breath, nausea, and laryngeal oedema.

Anaphylactoid reactions have been observed in particular in patients with renal insufficiency who are treated by haemodialysis, haemofiltration or haemodiafiltration using a membrane exchanger. They have been observed in the case of exchangers having membranes of different chemical compositions, either during a single use thereof or after several uses, when the exchangers, instead of being discarded after a single use, are re-used many times and are recycled after each use. Examples of exchangers whose first use has been accompanied by an adverse reaction are the dialysers which have a membrane of polymethylmethacrylate and polyacrylonitrile. Reactions associated with the reuse of dialysers with a membrane of cellulose acetate and polysulphone have also been well documented (see D. A.Pegues et al. "Anaphylactoid reactions associated with reuse of hollow-fiber hemodialysers and ACE inhibitors" Kidney International 42, 1232–1237 (1992).

Anaphylactoid reactions are attributed to an excessive concentration of a peptide substance, bradykinin, in the blood or plasma. One explanation which has been put forward to account for these adverse reactions in some patients undergoing blood treatment by extracorporeal circulation starts from the premise that the blood, when it comes into contact with the negatively charged surface of some blood treatment apparatuses, is the seat of a biological phenomenon, called activation of the contact phase, leading to the generation of active substances, kallikrein and factor XIII, from inactive substances, pre-kallikrein and factor XII, kallikrein having a catalytic effect on the production of factor XIIa, and vice versa. Now, bradykinin results from the conversion, effected by the kallikrein generated upon activation of the contact phase, of a plasma protein, namely kininogen of high molecular weight.

It should be emphasized that the activation of the contact phase seems to occur especially when a blood treatment device having a negatively charged surface is used, but without the patients experiencing the least discomfort as a result, if there are no interfering factors. Complications do sometimes occur in the presence of interfering factors such as, for example:

The presence, in the blood to be treated, of medicaments for combating high blood pressure by inhibiting the natural mechanism of vasoconstriction, which medicaments are generically designated by the term angiotensin converting enzymes or ACEs. These ACEs are also used for other therapeutic applications, especially for treating certain forms of cardiac insufficiency. Now, another effect of the ACEs is that of preventing the breakdown of bradykinin.

The dilution of the blood entering the dialyser filled with saline solution, and the concomitant lowering of the pH of the blood.

In order to avoid generation of bradykinin at a level greater than 4000 pg/ml, the European Patent Application no. 0,561,379 recommends bringing into contact with the blood or the plasma only those semi-permeable membranes having a limited surface charge density, namely a surface electrical charge greater than or equal to $-30$ $\mu$eq/g of polymer (i.e. $-30$ meq/kg of polymer).

It appears, however, that within the meaning of European Patent Application no. 0,561,379 the surface electrical charge is to be interpreted as the global ion capacity. Consequently, the said European Patent Application only concerns semi-permeable membranes having a limited charge density, and not semi-permeable membranes having a high density of negative charges, such as, for example, the membrane produced from a copolymer of acrylonitrile and sodium methallylsulphonate, and known by the trade name AN69.

Furthermore, in order to obtain membranes having a limited surface electrical charge, that is to say also a low global ion capacity, the said patent application proposes treating the polymer in such a way as to lower the ion capacity in the bulk. Now, it is of advantage not to modify the ion capacity of the membranes, since this capacity favours the adsorption of certain undesirable proteins, such as $\beta$2-microglobulin, mediators of inflammation, lipids, complement factors. This is particularly true in the case of membranes having a homogeneous, symmetrical structure.

Moreover, chemical compounds are known which have a substantial anti-protease activity characterized by an inhibitory action in the coagulation system, in the complement system, and in the kallikrein-kinin system (inhibition of plasma and tissue kallikreins). One example which may be mentioned is nafamostat mesylate (chemical name: 6-amidino-2-naphthyl-p-guanidinobenzoate dimethanesulphonate) marketed by the company TORII PHARMACEUTICAL.

Nafamostat mesylate is essentially used as an anticoagulant in extracorporeal circulations in cardiac surgery, in plasmapheresis, in anti-LDL apheresis, and in haemodialysis. The usage protocol generally followed and most often recommended is the following:

(a) addition of 20 mg of nafamostat mesylate in 500 ml of saline solution for rinsing the medical apparatus prior to use;

(b) continuous perfusion of nafamostat mesylate at a rate of 20 to 50 mg/hour.

Such a protocol involves the use of large quantities of nafamostat mesylate, generally more than 100 mg of nafamostat mesylate per haemodialysis session. One drawback of this compound is that it is much more costly than the traditional anticoagulants, such as heparin.

In addition, studies have shown that the results in terms of anticoagulation are not satisfactory when the nafamostat mesylate is used for haemodialysis with negatively charged membranes, such as membranes made of polymethylmethacrylate or polyacrylonitrile, in particular the membrane with the trade name AN69 from the company HOSPAL.

Studies have shown that these unsatisfactory results coincide with the strong adsorption of nafamostat mesylate on these membranes and that this adsorption leads to a decrease in the anticoagulant activity of this compound. This is evident in particular from the following publications:

Y. Tsubakihara et al. "Anticoagulant activity of FUT-175 in polyacrylonitrile membrane dialysers". [Abstract of the 9th annual meeting of the International Society of Blood Purification] Blood Purification 9, 1, 51–52 (1991).

O. Inagaki et al. "Study of the binding capacity of nafamostat mesylate (NM) to dialysis membranes". Artif. Org. 15, 4, 287 (1991).

O. Inagaki et al. "Adsorption of nafamostat mesylate by hemodialysis membranes". Artif. Org. 16, 6, 553–558 (1992).

In order to prepare a plasma having a low content of bradykinin, the Japanese Patent Application published on 13th December 1994 under no. 6-340536 recommends a medical apparatus in which the active adsorption element, with the task of adsorbing and eliminating the undesirable compounds of the plasma, is a carrier of anionic groups. In addition, this medical apparatus is provided with:

a means for mixing together an anti-protease agent, such as nafamostat mesylate, and plasma, before the latter is treated;

a means for perfusion of the anti-protease agent and plasma mixture on the active adsorption element; and a means for the adsorption and elimination of the undesirable compounds of the plasma with the aid of the active adsorption element.

The quantity of anti-protease solution introduced into this medical apparatus is between 10 $\mu$moles and 60 $\mu$moles per hour (i.e. approximately 5 to 30 mg/hour).

According to that patent application it is preferable to pre-treat the active adsorption element, before use, with a pre-treatment solution containing an anti-protease agent. In addition, in order to prevent the anti-protease agent from being damaged by the sterilization treatment, it is recommended to pre-treat the active adsorption element following the sterilization treatment. Also, in order to prevent the anti-protease agent m from being damaged by the ultraviolet rays, the heat or any other phenomenon which may arise during storage, it is recommended to pre-treat the active adsorption element just prior to its use, i.e. no more than 24 hours before use if it is stored at ambient temperature, and no more than 72 hours before use if it is stored at a lower temperature, between 2° C. and 8° C.

In the case where the plasma is treated in an intermittent manner by the active adsorption element, the patent application advises pre-treating this active element before the treatment of each plasma fraction.

Moreover, in order to avoid using excessively large quantities of anti-protease agent, the said patent application recommends choosing an active adsorption element whose quantity of anionic groups present at the surface is limited, that is to say is preferably between 0.5 $\mu$eq and 100 $\mu$eq per ml of swollen polymer of the active adsorption element, and again preferably between 1 $\mu$eq and 50 $\mu$eq per ml of swollen polymer of the active adsorption element (the term "swollen polymer" signifies the active adsorption element hydrated to the extent corresponding to clinical use).

A disadvantage of the process proposed by Japanese Patent Application no. 6-340536 is that it cannot be applied industrially, its implementation having to be carried out at the site of treatment.

In light of the above, it does not appear at present that a satisfactory solution, either in medical terms or in economic terms, has been provided for preventing the occurrence of anaphylactoid reactions in some patients undergoing treatment of the blood or plasma with the aid of a medical apparatus in which at least a part of the apparatus coming into contact with the blood or plasma has a surface density of electronegative charges.

One object of the invention is therefore to realize a medical apparatus with semi-permeable membrane for the extracorporeal treatment of the blood or plasma, which has two characteristics which to date have been regarded as being contradictory, namely a high global ion capacity (which at one and the same time contributes to the biocompatibility of some materials and is a factor triggering the activation of the contact phase) and the capability of preventing the adverse effects of activation of the contact phase.

In other words, one object of the invention is a medical apparatus with semi-permeable membrane for the extracorporeal treatment of blood or plasma, in which the membrane is able to prevent the adverse effects of activation of the contact phase and is to all intents and purposes insensitive to oxidizing agents and radiation, in particular gamma radiation, so that it can be sterilized.

Another object of the invention is a medical apparatus with semi-permeable membrane for the extra-corporeal treatment of blood or plasma, which is substantially stable on storage and at the time of its use.

Finally, one object of the invention is a medical apparatus with semi-permeable membrane for the extra-corporeal treatment of blood, which apparatus can be applied industrially, that is to say is ready for use and does not require any special manipulation on the part of the user of the medical apparatus for the purposes of preventing the adverse effects of activation of the contact phase.

To achieve these various objects, the present invention proposes a medical apparatus for the extracorporeal treatment of blood or plasma, comprising a semi-permeable membrane consisting of at least one electronegative polymer, such that the surface of the semi-permeable membrane has negative electric charges, this apparatus being characterized in that, before sterilization of the apparatus, and before or after the formation of the membrane, at least one cationic and anti-protease agent is incorporated in at least one part of the membrane, this agent undergoing bulk adsorption or semi-bulk adsorption in the membrane and/or being bound by an ionic interaction with the electronegative sites of the membrane.

The term "extracorporeal treatment of blood" signifies, for example, haemodialysis, haemofiltration or haemodiafiltration, and plasmapheresis.

The term "semi-permeable membrane" signifies a flat membrane or a bundle of hollow fibres. Thus, the apparatus according to the invention generally comprises two compartments separated by the semi-permeable membrane.

The term "bulk adsorption or semi-bulk adsorption" signifies binding of the cationic and anti-protease agent by electrostatic links, in particular ionic links, within the thickness or on the surface of the membrane.

Surprisingly, it has been found that it is possible to prevent the adverse consequences of activation of the contact phase, which can arise occasionally during treatment of the biological fluids intended to be returned to the human body, such as plasma or blood, with semi-permeable and anionic membranes, by incorporating into these membranes, before sterilization, at least one cationic agent which has an anti-protease action vis-à-vis the kallikrein-kinin contact system.

In addition, the medical apparatus according to the invention does not require any special manipulation on the part of the user of the medical apparatus for the purposes of preventing the adverse effects of activation of the contact phase, such as treating the membrane with an anti-protease agent before the medical treatment and/or continuously perfusing anti-protease agent during the medical treatment.

The preferred cationic and anti-protease agent is nafamostat mesylate.

One advantage of nafamostat mesylate, which is of prime importance for medical apparatuses for the extracorporeal treatment of blood or plasma, resides in the fact that incorporating small quantities of this agent in a semi-permeable membrane having a high global ion capacity makes it possible to prevent the adverse effects of activation of the contact phase. Thus, as indicated below (in Example 5), 7 mg of nafamostat mesylate per m of total surface area of the AN69 membrane are sufficient, on condition that the recommendations indicated below for using the apparatuses are followed, which may vary according to the specific features relating to manufacture of the medical apparatus.

In accordance with the invention, the semi-permeable membrane used to realize the medical apparatus for the extracorporeal treatment of blood or plasma, and with which it is possible to prevent the adverse effects of activation of the contact phase, consists of a combination of at least one electronegative polymer and of at least one cationic and anti-protease agent.

In addition, the invention is particularly well adapted to the medical apparatuses in which the semi-permeable membrane has a high global ion capacity.

The invention is particularly well adapted to the medical apparatuses in which the semi-permeable membrane has a negative charge density greater than 100 $\mu$eq per ml of swollen polymer (by way of reference, the electro-negative polymer used to realize the AN69 membrane has a negative charge density equal to approximately 180 $\mu$eq per ml of swollen polymer) as measured by the conventional method of ion exchange.

The semi-permeable membrane is advantageously a flat membrane or a bundle of hollow fibres consisting of at least one electronegative polymer which can be the homopolymer or a copolymer of acrylonitrile.

Examples of acrylonitrile copolymers which may be mentioned are:

(1) a copolymer of acrylonitrile and of at least one anionic or anionizable monomer, containing, where appropriate, units originating from at least one other monomer with olefinic unsaturation capable of being copolymerized with acrylonitrile, or (2) a copolymer of acrylonitrile and of at least one anionic or anionizable monomer and at least one non-ionic and non-ionizable monomer.

Some of these macromolecular compounds, as well as the various monomers which can be kept as basic materials, and their production, are described in U.S. Pat. No. 4,545,910 reissued under no. Re.34239.

Of these macromolecular compounds, those for which the medical apparatus according to the invention is particularly well adapted are defined above under (1). In particular, the invention is especially well suited to the compounds for which the anionic or anionizable comonomer is olefinically unsaturated and carries anionic groups chosen from among the sulphonate, carboxyl, phosphate, phosphonate and sulphate groups, and still more especially when this comonomer is sodium methallylsulphonate.

Of course, the precise nature of the counter-ion of the anionic groups is not essential to the satisfactory functioning of the invention.

Of the monomers with olefinic unsaturation which are capable of being copolymerized with acrylonitrile, there may be mentioned the alkyl acrylates and, in particular, methyl acrylate.

The invention also relates to:
  processes for preparation of a flat membrane or of a hollow fibre, used for realizing the semi-permeable membrane of the medical apparatus for the extracorporeal treatment of blood or plasma;
  a process for production of the medical apparatus for the extracorporeal treatment of blood or plasma.

A first process for preparation of a flat membrane comprises the steps of:
preparing a solution comprising:
  at least one electronegative polymer,
  at least one solvent of the electronegative polymer,
  if appropriate, at least one non-solvent of the electronegative polymer,
extruding this solution through a flat die;
after the extrusion, solidifying to form the flat semi-permeable membrane by a process of solidification by phase inversion through contact with a liquid which is chemically inert vis-à-vis the electronegative polymer, this liquid containing at least one anti-protease and cationic agent, in the dissolved state;
optionally stretching the flat semi-permeable membrane obtained, and
washing the semi-permeable membrane obtained.

A second process for preparation of a flat membrane comprises the steps of:
preparing a solution comprising:
  at least one electronegative polymer,
  at least one solvent of the electronegative polymer,
  if appropriate, at least one non-solvent of the electronegative polymer,
extruding this solution through a flat die;
after the extrusion, solidifying to form the semi-permeable membrane by a process of solidification by phase inversion through contact with a fluid which is chemically inert vis-à-vis the electronegative polymer;
optionally stretching the flat semi-permeable membrane obtained, and
washing the resulting semi-permeable membrane with a washing solution containing at least one anti-protease and cationic agent, in the dissolved state.

A third process for preparation of a hollow fibre comprises the steps of:
preparing a solution comprising:
  at least one electronegative polymer,
  at least one solvent of the electronegative polymer,
  if appropriate, at least one non-solvent of the electronegative polymer,
extruding this solution so as to form a hollow fibre and at the same time solidifying the resulting hollow fibre by a process of phase inversion through partial or total contact of the extruded product with a centering fluid which is chemically inert vis-à-vis the electronegative polymer and which contains at least one anti-protease and cationic agent in the dissolved state;
optionally stretching the hollow fibre obtained, and
washing the hollow fibre obtained.

A fourth process for preparation of a hollow fibre comprises the steps of:
preparing a solution comprising:
  at least one electronegative polymer, at least one solvent of the electronegative polymer,
if appropriate, at least one non-solvent of the electronegative polymer,
extruding this solution so as to form a hollow fibre and at the same time solidifying the resulting hollow fibre by a process of phase inversion through partial or total contact of the extruded product with a centering fluid which is chemically inert vis-à-vis the electronegative polymer;
optionally stretching the hollow fibre obtained, and
washing the resulting hollow fibre with a washing solution containing at least one anti-protease and cationic agent in the dissolved state.

The other conventional operating conditions for the four processes mentioned above can be found in U.S. Pat. No. 4,749,619 (process by gelation) or in U.S. Pat. No. 4,056,467 (process by coagulation).

In accordance with the invention, a medical apparatus is produced with one of the flat membranes or hollow fibres obtained by means of one of the above mentioned processes. The principal production steps are the following:
preparing a semi-permeable membrane of defined surface area from the flat membrane or the hollow fibre, the hollow fibre being fashioned as a bundle of hollow fibres;
assembling the various components of the medical apparatus, in particular mounting the flat membrane or the bundle of hollow fibres in a casing, and, if appropriate, fixing end caps onto the casing.

The invention also relates to a process for production of a medical apparatus for the extracorporeal treatment of blood or plasma, comprising a semi-permeable membrane delimiting two compartments inside a casing, the membrane consisting of at least one electronegative polymer and having a surface with negative electric charges, this process comprising the steps of:
preparing a flat membrane or a hollow fibre;
assembling the various components of the apparatus, in particular mounting a flat, semi-permeable membrane or a bundle of hollow fibres in a casing;
preparing a solution containing the cationic and anti-protease agent in the dissolved state, the pH of this solution being acidic or neutral (i.e. pH less than or equal to 7);
before sterilizing the medical apparatus, bringing this solution into contact with at least one part of the semi-permeable membrane, then purging the apparatus of this solution.

The solution comprising the cationic and anti-protease agent is preferably brought into contact with at least one part of that surface of the membrane situated on the side of compartment of the apparatus which is intended to receive the blood or plasma from the patient.

According to a first embodiment of the invention, the step of bringing the solution into contact with the membrane consists in circulating the solution comprising the cationic and anti-protease agent from one end of the blood compartment to the other, then reversing the direction of circulation of the solution in such a way that each end of the compartment is in contact with the solution containing the anti-protease agent at the preparation concentration.

An important advantage of this first embodiment of the invention resides in the fact that the two access tubes to the blood compartment i are equivalent insofar as one can be used for blood inlet and the other for blood outlet, or vice versa. In addition still in the context of this first embodiment of the invention, the quantity of cationic and anti-protease agent to be incorporated in the semi-permeable membrane is small. Thus, as indicated below (in Example 5), 7 mg of nafamostat mesylate per $m^2$ of total surface area of the AN69 membrane are sufficient to avoid causing an increase in the level of plasma kallikreins in a diluted plasma.

According to a second embodiment of the invention, the step of bringing the solution comprising the cationic and anti-protease agent into contact with the membrane from one end of the blood compartment to the other consists in circulating the solution in a single direction of circulation which is the opposite of that intended for the blood or plasma from the patient.

In practice, in order to facilitate the use of the medical apparatus produced according to this second embodiment of the -invention, before bringing a solution containing the cationic and anti-protease agent into contact with the membrane, the inlet and the outlet of the compartment of the apparatus which is intended to receive the blood or plasma from the patient are located so that the inlet for the solution of cationic and anti-protease agent is used as the blood outlet and the outlet for the solution of the cationic and anti-protease agent is used as the blood inlet.

Preferably, the flow rate of the solution comprising the cationic and anti-protease agent which is circulated in a single direction, the opposite of that intended for the blood and plasma from the patient, is low. Thus, in the aforementioned case of nafamostat mesylate and the AN69 membrane, it is advantageous to limit the flow rate of the solution to a value of less than 100 ml/min, and more preferably of the order of 50 ml/min or less.

One sterilization technique which can be employed without damaging the cationic and antiprotease agent, and without causing desorption of this agent, is that of sterilization by gamma irradiation.

DETAILED DESCRIPTION OF THE DRAWINGS

FIGS. 1–4 are described adequately above.

Figure 5:
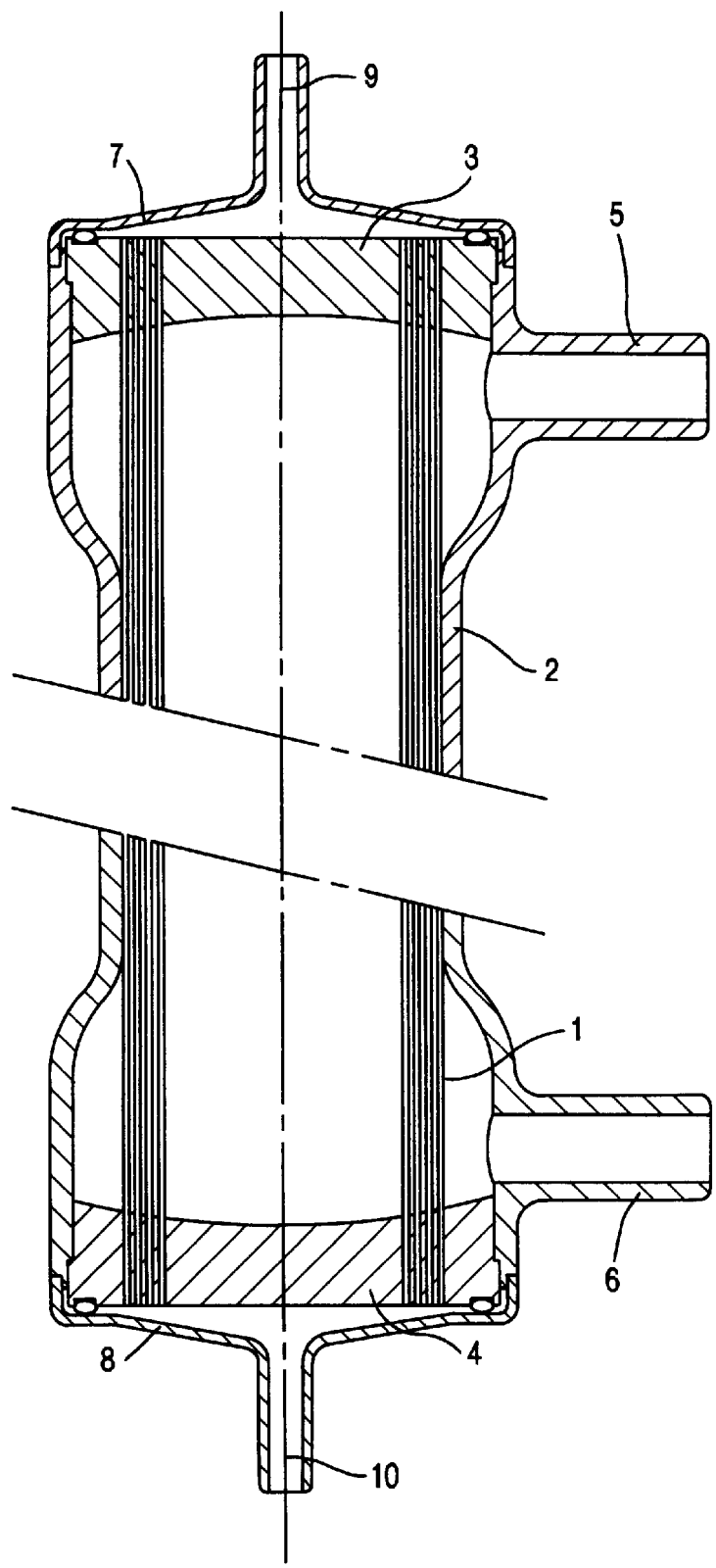
FIG. 5 is a vertical cross sectional view of a preferred embodiment of apparatus of the invention.

A FIG. 5 represents a membrane exchanger comprising two compartments which are separated by a semi-permeable membrane composed of a (partially represented) bundle 1 of semi permeable hollow fibers. The bundle 1 is secured within a tubular housing 2 at both ends by means of two disks 3,4 of potting material. The disks 3,4 tie up the fibers together and they delimit between them within the housing 2 a fluid-tight compartment to which two pipes 5,6 give access, which are perpendicular to the longitudinal axes 9 of the housing 2. Two end caps 7,8 are respectively secured at the ends of the housing 2. Each end cap 7,8 comprises an axial access pipe 9,10. The blood compartment of this exchanger is composed of the lumens of the hollow fibers and of the inner space delimited between the end caps 7,8 and the disks 3,4 of potting material.

Without further elaboration, it is believed that one skilled in the art can, using the preceding description, utilize the present invention to its fullest extent. The following working examples are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

EXAMPLE 1

A dialyser was produced in accordance with the invention by the company HOSPAL INDUSTRIE, Meyzieu (Rhbne), France. A hollow fibre was produced by the following gelation process: a mixture of copolymer of an acrylonitrile and sodium methallylsulphonate (35% by mass; 580 mEq/kg of dry polymer), dimethylformamide (52% by mass) and glycerol (13% by mass) was prepared. This mixture was brought to 130° C. and was extruded through an annular die by means of a coupled extrusion/pumping device. The centering fluid used to form the internal cavity of the fibre was dry nitrogen. On leaving the die, the fibre was received in a bath containing a mixture of water and hydrogen peroxide at 10° C., and was then stretched in a water bath at 95° C. (length quadrupled). Finally, the fibre was plasticized with a mixture of water and glycerol (60% by mass). The electric charge density or global ion capacity of this hollow fibre was 180 µeq/ml of swollen copolymer.

A bundle of approximately 9000 hollow fibres was prepared. The useful surface area of the membrane in the wet state was approximately 1.3 m². The total surface area in contact with the blood is 1.43 m² This bundle was inserted into a tubular casing made of polycarbonate in which it was fixed at its two ends by a disc of polyurethane adhesive trapping the fibres over part of their length. The two discs of adhesive delimit between each other an impervious compartment in which, when the dialyser is in use, a dialysis liquid is circulated via two tubes. A second compartment is delimited by the inside of the fibres and two end caps, which are each equipped with an access tube, fixed to the ends of the casing. When the dialyser is in use, it is in this second compartment that the patient's blood is circulated.

A solution was prepared which consisted of demineralized water in which nafamostat mesylate (marketed under the name FUTHAN by the company TORII PHARMACEUTICAL) was dissolved in a concentration of 20 mg/litre. The pH of this solution is acidic (i.e., equal to 4.3).

After assembly of the various components of the dialyser (casing, bundle of fibres, and end caps) and before sterilization, a litre of this solution was circulated at a flow rate of 300 ml/min in the blood compartment of the dialyser, in a single direction of circulation, the opposite of that intended for the blood or the plasma, and the dialyser was then purged of this solution.

Two days later the dialyser was sterilized by gamma irradiation.

To measure the efficacy of this production process, the dialyser thus produced was subjected to the following test:

A biological fluid was prepared which was capable of stimulating production of kallikreins (KK) upon contact with this membrane negatively charged at the surface. The biological fluid used for the test consisted of human platelet-poor plasma, diluted to 5%. Two fluids of this liquid were circulated in a closed circuit in the dialyser at a flow rate of 100 ml/min for six hours: the direction of circulation of biological liquid in the blood compartment of the dialyser was the opposite of that of the solution containing the nafamostat mesylate. The plasma kallikreins were measured in samples of fluid taken at a time interval (t) using a conventional chromogenic test, using the substrate S 2302 from the company BIOGENIC. It is clearly evident from the attached FIG. 1 that the dialyser produced in accordance with the invention does not cause an increase in the level of plasma kallikreins in a diluted plasma.

In this regard, it is considered in the present application that, taking into account the chromogenic test used, and its sensitivity, there is no significant increase in the level of kallikreins if its concentration remains below about 20 units per litre, or still better below about 10 units per litre.

EXAMPLE 2

This example illustrates the importance of the direction of circulation of the biological liquids when the incorporation of nafamostat mesylate was produced by circulation, in a single direction, of a solution containing this agent in the blood compartment.

To do this, the production and evaluation test conditions in Example 1 were reproduced while modifying only the direction of circulation of the biological liquid so that it is the same as the direction of circulation of the solution consisting of demineralized water and mesylate.

Figure 1:
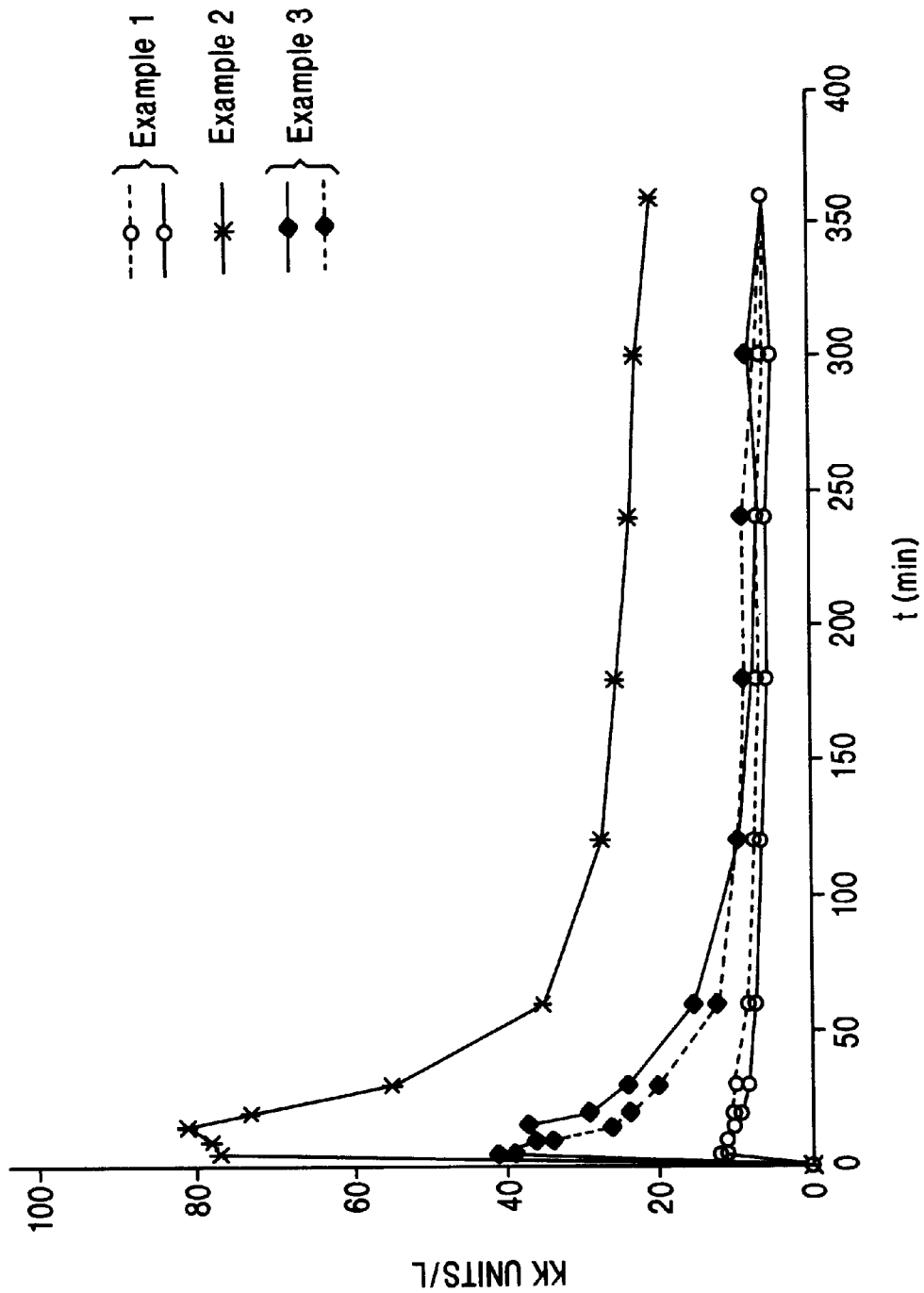
FIG. 1 illustrates the values of the concentration of bradykinin as a function of the time in the operation of examples 1, 2 and 3.

An increase in the level of plasma kallikreins in a diluted plasma is clearly evident in the attached FIG. 1.

EXAMPLE 3

By way of comparison, a conventional chromogenic test carried out under the conditions of Example 1 was conducted using a dialyser of the type PAN 17 DX produced by the company ASAHI MEDICAL CO (bundle of hollow fibres made from a polyacrylonitrile; useful surface area 1.7 m²).

It is clearly evident from the attached FIG. 1 that this dialyser, whose membrane has negative electric charges at the surface, causes a considerable increase in the level of plasma kallikreins in a diluted plasma.

EXAMPLES 4 AND 5

These examples illustrate various medical apparatuses in accordance with the invention, in which the quantity of nafamostat mesylate to be incorporated in the membrane was varied.

To do this, most of the production and evaluation conditions in Example 1 were reproduced, while modifying only the following production conditions:

the proportion (c) of mesylate in the demineralized water;
the details of the circulation of the nafamostat mesylate solution in the blood compartment of the dialyser: circulating half the solution (500 ml) from one end of the blood compartment to the other, then circulating the other half of the solution in the opposite direction so that each end of the blood compartment is in contact with the solution containing the nafamostat mesylate solution at its preparation concentration.

The other particular conditions in Examples 4 and 5 are collated in Table (I) below.

| EXAMPLE | 4 | 5 |
| --- | --- | --- |
| Proportion (c) of nafamostate mesylate (mg/l) | 25 | 10 |
| Proportion of nafamostate mesylate incorporated per $m^2$ of membrane (mg/$m^2$) | 17.5 | 7 |

Figure 2:
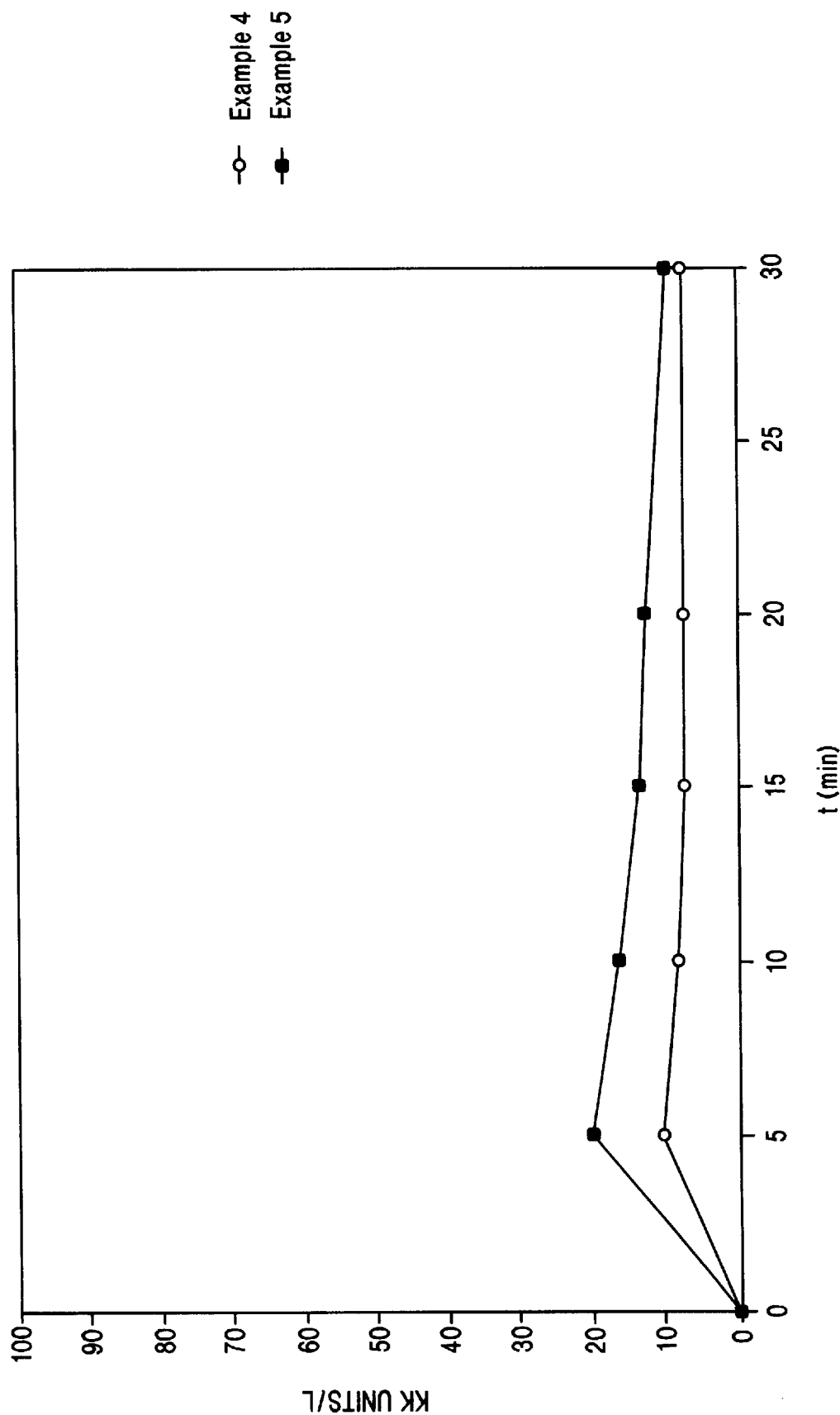
FIG. 2 illustrates the values of the concentration of bradykinin as a function of the time in the operation of examples 4 and 5.

It is clearly evident from the attached FIG. 2 that the dialysers in Examples 4 and 5, produced in accordance with the invention, do not cause an increase in the level of plasma kallikreins in a diluted plasma.

EXAMPLE 6 TO 8

These examples illustrate the influence of the pH of the nafamostat mesylate solution in the manufacture of the medical apparatuses in accordance with the invention.

To do this, most of the production and evaluation conditions mentioned in Example 1 were reproduced, while modifying only the composition of the nafamostat mesylate solution as follows: a solution was prepared which consisted of demineralized water in which one or more chemical compounds were added to control the pH of the solution. As soon as the desired pH was reached, nafamostat mesylate was dissolved in a proportion of 20 mg/litre. The following table specifies the preparation conditions for the nafamostat mesylate solution.

| EXAMPLE | 6 | 7 | 8 |
| --- | --- | --- | --- |
| Chemical compounds used to control the pH of the nafamostate mesylate (NM) solution | $Na_2HPO_4$ (10 mmoles/liter) + HCl | $Na_2HPO_4$ (10 mmoles/liter) + HCl | $Na_2HPO_4$ (10 mmoles/liter) |
| pH of the solution | 4 | 7 | 9 |

Figure 3:
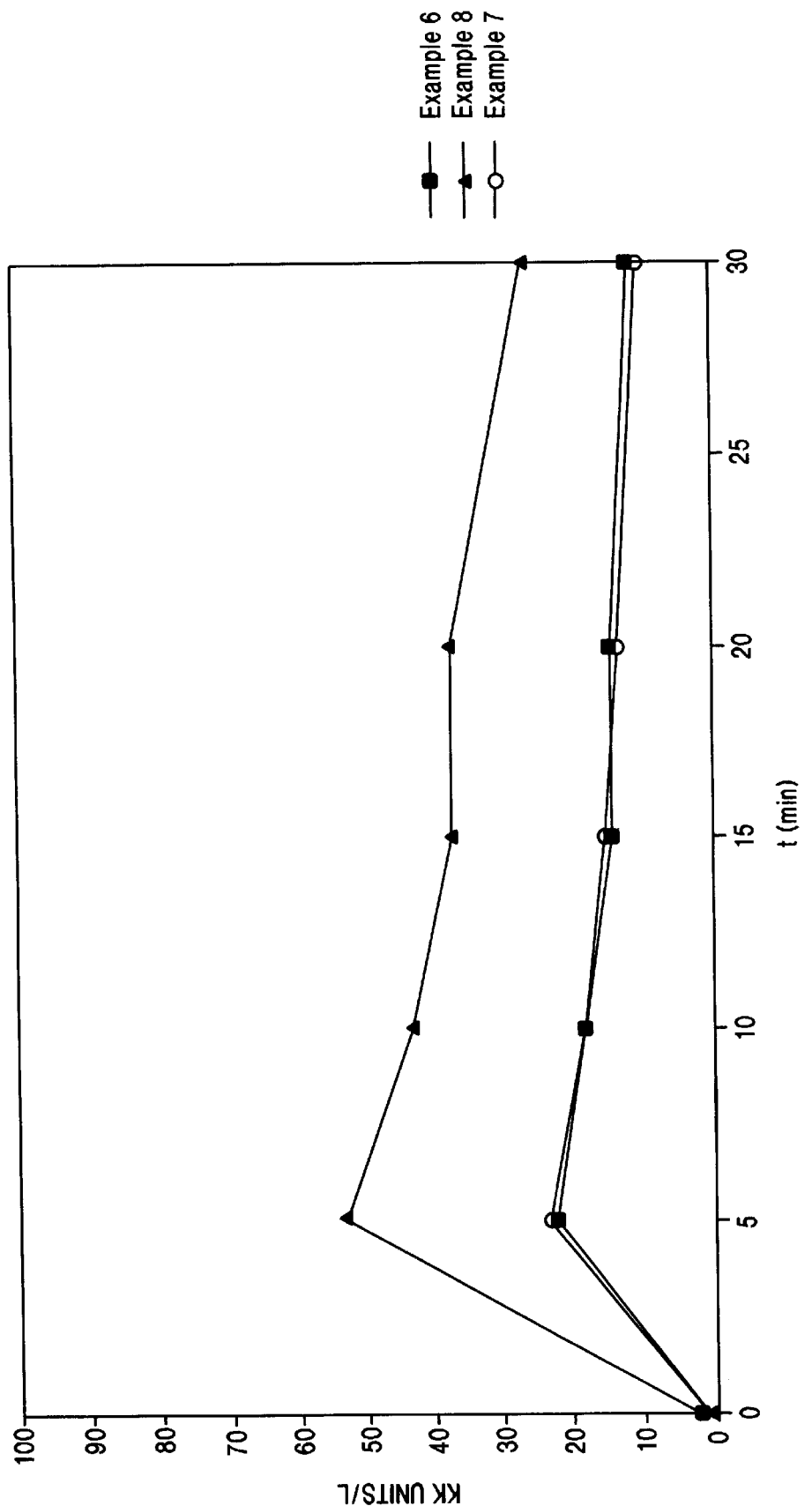
FIG. 3 illustrates the values of the concentration of bradykinin as a function of the time in the operation of examples 6, 7 and 8.

It is clearly evident from the attached FIG. 3 that, in the production of the dialysers in accordance with the invention, it is recommended to use a nafamostat mesylate solution with neutral or acidic pH (Examples 6 and 7) so that the dialysers do not cause an increase in the level of plasma kallikreins in a diluted plasma.

EXAMPLES 9 AND 10

Examples 9 and 10 illustrate the influence of the flow rate of the nafamostat mesylate solution in the production of the medical apparatuses in accordance with the invention.

To do this, most of the production and evaluation conditions mentioned in Example 1 were reproduced, while modifying only the flow rate of the solution of 1 litre of nafamostat mesylate circulated in the blood compartment of the dialyser in a single direction of circulation, to reduce it to a value of 50 ml/min.

In addition, in the context of Example 9, the direction of circulation of the biological liquid was the opposite of that of the solution containing the nafamostat mesylate, whereas in the context of Example 10, the direction of circulation of the biological liquid and of the solution containing the nafamostat mesylate were the same.

Figure 4:
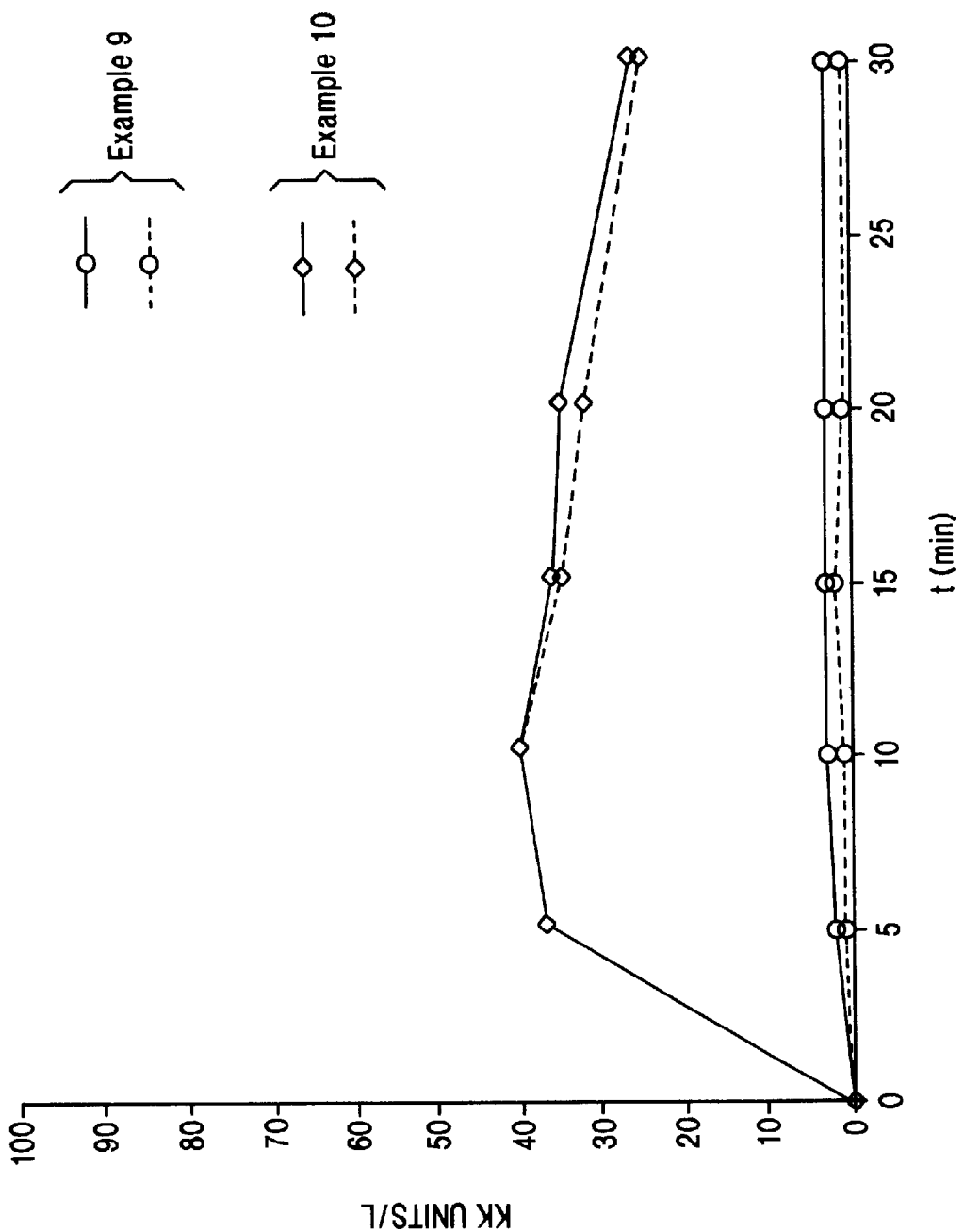
FIG. 4 illustrates the values of the concentration of bradykinin as a function of the time in the operation of examples 9 and 10.

The results of the conventional chromogenic tests carried out under the conditions of Example 1 were reported in the attached FIG. 4: the black diamonds correspond to two identical series of Example 10 and the circles correspond to two identical series of Example 9.

It is clearly evident from FIG. 4 that a low flow rate (here 50 ml/min) leads to results which, in terms of the increase in the level of plasma kallikreins in a diluted plasma, are highly advantageous when compared with those obtained with a higher flow rate (i.e., 300 ml/min, in Example 1).

EXAMPLE 11

Evaluation of the hydraulic permeability, of the urea clearance and of the vitamin B12 and myoglobin transmittance of three dialysers A, B, C produced under the conditions in Example 1.

Dialysis Bath Permeability (UF)

This corresponds to the dialysis bath flow rate through the membrane under the following experimental conditions:

dialysis bath flow rate in the inner compartment of the dialyser: 300 ml/min;

transmembrane pressure: 85 mmHg.

Urea Clearance

This indicates the purification efficiency of the medical apparatus by diffusion of the solids from the blood or plasma to the dialysate through the membrane, and is defined as the ratio of the flow of solutes through the membrane to the concentration of the solutes at the inlet of the apparatus. It is determined in the context of an in vitro measurement protocol, in which the blood is replaced by a solution of urea in the dialysate, the fluids are circulated in countercurrent and with a temperature regulated to 37° C. Its value is given for operating conditions representative of those employed in CAVHD or CVVHD, i.e., for a blood flow rate Qs of 100 ml/min, a dialysate flow rate Qd of 2 l/h and an ultrafiltration rate Qf of 0 ml/min.

Transmittance T

The transmittance represents the fraction of molecules which passes by convection through the pores in the membrane. It is defined for a given molecule as the ratio of the concentration of the solutes in the ultrafiltrate to its average concentration in the non filtered fraction of the liquid. The operating conditions are as follows:

the vitamin B12 concentration: 30 mg/l;

ultrafiltration rate: 60 ml/min.

The performance of the three dialysers A, B and C in accordance with the invention which were tested are collated in the following table.

| | PERFORMANCE | | | |
| --- | --- | --- | --- | --- |
| Dialyser | UF (ml/h.$m^2$. mmHg) | Urea clearance (ml/min.) | Myoglobin transmittance | Vitamin B12 transmittance |
| A | 53.8 | 231 | 0.69 | 1 |
| B | 53.0 | 234 | 0.68 | 1 |
| C | 53.0 | 231 | 0.68 | 1 |

The performance of the dialysers A, B and C is excellent and equivalent to that obtained with a conventional dialyser comprising an AN69 membrane with an equivalent useful surface area.

The preceding examples can be repeated with similar success by substituting the generically or specifically described reactants and/or operating conditions of this invention for those used in the preceding examples.

The entire disclosure of all applications, patents and publications, cited above, and of corresponding French applications 96/05189 and 96/09340, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Medical apparatus for the extracorporeal treatment of blood or plasma, comprising a semi-permeable membrane comprising at least one electronegative polymer, such that the surface of the semi-permeable membrane has negative electric charges, wherein the semi-permeable membrane has a negative electric charge density greater than 100 $\mu$eq per ml of swollen polymer wherein, before sterilization of the apparatus, at least one cationic and anti-protease agent is incorporated in at least one part of the membrane, wherein the anti-protease agent is present in sufficient quantities to prevent activation of the kallikrein-kinin system during treatment of blood or plasma, said agent being bound in the membrane by bulk adsorption or semi-bulk adsorption and/or being bound by an ionic interaction with the electronegative sites of the membrane.

2. Medical apparatus according to claim 1, wherein the cationic and anti-protease agent is nafamostat mesylate.

3. Medical apparatus according to claim 1, wherein the electronegative polymer is polyacrylonitrile.

4. Medical apparatus according to claim 1, wherein the electronegative polymer is a copolymer of acrylonitrile and at least one other monomer with olefinic unsaturation capable of being copolymerized with the acrylonitrile.

5. Medical apparatus according to claim 1, wherein the electronegative polymer is a copolymer of acrylonitrile, at least one anionic or anionizable monomer, and at least one non-ionic and non-ionizable monomer.

6. Medical apparatus according to claim 4, wherein the monomer with olefinic unsaturation, capable of being copolymerized with the acrylonitrile, carries anionic groups that are sulphonate, carboxyl, phosphate, phosphonate or sulphate groups.

7. Medical apparatus according to claim 6, wherein the anionic groups comprise sodium methallylsulphonate.

8. Medical apparatus according to claim 2, wherein the electronegative polymer is polyacrylonitrile.

9. An apparatus according to claim 1, wherein the apparatus is in an unsterilized form.

10. An apparatus according to claim 1, wherein the apparatus is in a sterilized form.

11. In a method of conducting hemodialysis in a medical apparatus, the improvement comprising conducting hemodialysis with a medical apparatus so as to prevent activation of the kallikrein-kinin system said medical apparatus being in sterilized form and comprising a semi-permeable membrane comprising at least one electronegative polymer, such that the surface of the semi-permeable membrane has negative electric charges, this apparatus being characterized in that, before sterilization of the apparatus, at least one cationic and anti-protease agent is incorporated in at least one part of the membrane, wherein the anti-protease agent is present in sufficient quantities to prevent activation of the kallikrein-kinin system during treatment of blood or plasma, said agent being bound in the membrane by bulk adsorption or semi-bulk adsorption and/or being bound by an ionic interaction with the electronegative sites of the membrane.

12. A method according to claim 11, wherein the semi-permeable membrane has a negative electric charge density greater than 100 $\mu$eq per ml of swollen polymer.

13. A method of conducting hemodialysis according to claim 1, wherein the electronegative polymer is polyacrylonitrile, and the at least one cationic and anti-protease agent is nafamostat mesylate.

14. A method according to claim 11, wherein the electronegative polymer is polyacrylonitrile.

15. A method according to claim 11, wherein the electronegative polymer is a copolymer of acrylonitrile and at least one other monomer with olefinic unsaturation capable of being copolymerized with the acrylonitrile.

16. A method according to claim 11, wherein the electronegative polymer is a copolymer of acrylonitrile, at least one anionic or anionizable monomer, and at least one non-ionic and non-ionizable monomer.

17. A method according to claim 15, wherein the monomer with olefinic unsaturation, capable of being copolymerized with the acrylonitrile, carries anionic groups that are sulphonate, carboxyl, phosphate, phosphonate or sulphate groups.

* * * * *